Figure 1:
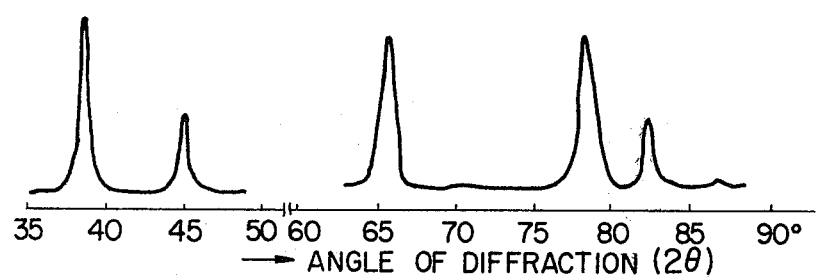

United States Patent [19]

Aoshima et al.

[11] 4,356,316

[45] Oct. 26, 1982

[54] PROCESS FOR PRODUCING UNSATURATED CARBOXYLIC ESTERS

[75] Inventors: Atsushi Aoshima, Yokohama; Toshiaki Murofushi, Fuji, both of Japan

[73] Assignee: Asahi Kasei Kogyo Kabushiki Kaisha, Osaka, Japan

[21] Appl. No.: 236,956

[22] Filed: Feb. 23, 1981

[30] Foreign Application Priority Data

Mar. 5, 1980 [JP] Japan .................................. 55-26759
Apr. 22, 1980 [JP] Japan .................................. 55-53154

[51] Int. Cl.³ ............................................. C07C 67/39
[52] U.S. Cl. .................................. 560/208; 252/439; 252/434; 252/435; 252/436; 252/430; 252/437; 252/455 R; 252/456; 252/457; 252/458; 252/460
[58] Field of Search ................. 560/208; 568/470, 478

[56] References Cited

U.S. PATENT DOCUMENTS

| | | | |
|---|---|---|---|
| 3,485,877 | 12/1969 | Hargis et al. ........................ | 568/478 |
| 3,658,886 | 4/1972 | Sennewald et al. ................. | 560/208 |
| 3,925,463 | 12/1975 | Ferlazzo et al. .................... | 560/208 |
| 4,248,019 | 2/1981 | Tamura et al. ...................... | 560/208 |

OTHER PUBLICATIONS

Kurakina, T. V. et al., *Chemical Abstracts*, vol. 86, (1977), #83233c.

*Primary Examiner*—Natalie Trousof
*Assistant Examiner*—L. Hendriksen
*Attorney, Agent, or Firm*—Sprung, Horn, Kramer & Woods

[57] ABSTRACT

A process for producing an ester of acrylic or methacrylic acid by oxidizing propylene or isobutylene in the liquid phase in the presence of a straight chain lower alcohol and molecular oxygen, characterized by carrying out the reaction in the presence of:

(1) a catalyst consisting of palladium and at least one metal selected from the group consisting of lead, bismuth, thallium, tellurium and mercury, preferably an intermetallic compound of palladium and said metal;

(2) at least one compound selected from the group consisting of mineral acids, heteropoly-acids, heteropoly-acid salts, molybdic acid and organic sulfonic acids, preferably heteropoly-acids or their salts; and (3) optionally, at least one compound selected from the group consisting of alkali metal compounds and alkaline earth metal compounds.

According to this process, the activity of catalyst is high even in a reaction at low temperatures, the amount of by-product is small and the objective ester can be produced with a high selectivity.

18 Claims, 2 Drawing Figures

ANGLE OF DIFFRACTION (2θ)

ANGLE OF DIFFRACTION (2θ)

PROCESS FOR PRODUCING UNSATURATED CARBOXYLIC ESTERS

This invention relates to a process for producing an ester of acrylic acid or methacrylic acid, and more particularly, to a process for producing an acrylic ester or a methacrylic ester by oxidizing propylene or isobutylene in the liquid phase in the presence of (1) a catalyst consisting of palladium and at least one metal selected from the group consisting of lead, bismuth, thallium, tellurium and mercury and (2) at least one compound selected from the group consisting of mineral acids, heteropoly-acids, salts of heteropoly-acids, molybdic acid and organic sulfonic acids.

As a process for producing an acrylic or methacrylic ester in one step by the liquid phase oxidation of propylene or isobutylene, there has hitherto been known the process mentioned in Japanese Patent Publication No. 37,010/73 in which only palladium metal is used. However, the process using palladium metal had disadvantages that the ester formation activity of the catalyst was as low as 1.7 g ester/g-Pd.hr at 140° C. and the selectivity was as low as 10% or less. Further, even if the palladium metal catalyst was used in the presence of a strong acid, the ester formation activity of the catalyst was still so low that the catalyst has no practical value. Further, if a catalyst consisting of palladium and at least one metal selected from the group consisting of lead, bismuth, thallium, tellurium and mercury was used, the ester formation activity of the catalyst was very low unless it was used in the presence of a strong acid.

The present inventors have conducted extensive research with the aim of realizing a high ester formation activity and obtaining the ester with a high selectivity. As a result, it has unexpectedly been found that the ester formation activity can be greatly improved (for example, 18 g ester/g-Pd.hr at 80° C.) by using a catalyst consisting of palladium and at least one metal selected from the group consisting of lead, bismuth, thallium, tellurium and mercury in the presence of at least one compound selected from the group consisting of mineral acids, heteropoly-acids, heteropoly-acid salts, molybdic acid and organic sulfonic acids.

According to this invention, there is provided a process for producing an ester of acrylic or methacrylic acid by oxidizing propylene or isobutylene in the liquid phase in the presence of a straight chain lower alcohol and molecular oxygen, characterized by carrying out the reaction in the presence of:
(1) a catalyst consisting of palladium and at least one metal selected from the group consisting of lead, bismuth, thallium, tellurium and mercury;
(2) at least one compound selected from the group consisting of mineral acids, heteropoly-acids, heteropoly-acid salts, molybdic acid and organic sulfonic acids; and
(3) optionally, at least one compound selected from the group consisting of alkali metal compounds and alkaline earth metal compounds.

According to this invention, the catalyst activity is high even when the reaction is carried out at low temperatures, the amount of by-products such as carbon dioxide is small, and an unsaturated carboxylic ester can be produced with a high selectivity.

The straight chain lower alcohols used in this invention are methanol, ethanol, 1-propanol and 1-butanol, among which methanol is particularly preferable.

Though the amount of propylene or isobutylene used in this invention is not critical, it is preferably 1 or less in terms of molar ratio to said straight chain lower alcohol.

The molecular oxygen referred to in this invention can be used in the form of pure oxygen gas or a gaseous mixture obtained by diluting oxygen gas with a diluent inert to the reaction such as nitrogen, helium, carbon dioxide gas or the like, and air may, of course, be used as the geseous mixture. Though the amount of oxygen allowed to exist in the reaction system is not critical, it is preferably not smaller than the stoichiometric amount necessary to the reaction. Usually, it is ⅓ to 5 times the stoichiometric amount.

The catalyst used in this invention consists of palladium and at least one metal selected from the group consisting of lead, bismuth, thallium, tellurium and mercury. It is usually preferable that the catalyst is in the solid catalyst form. These catalysts are required to be in a reduced state or to be converted to a reduced state under the conditions of the reaction. Preferably, catalysts in which palladium forms an intermetallic compound with at least one member selected from the group consisting of lead, bismuth, thallium, tellurium and mercury are used. It is particularly preferable to use an intermetallic compound of palladium with lead and/or bismuth. Though these catalysts do not necessarily require the use of a carrier, they are preferably used in the reaction after being supported on a known carrier such as silica, alumina, active charcoal, titania or the like. It is particularly preferable to select a ratio of palladium to said other element from the range in which the intermetallic compound is formed easily. For this purpose, palladium is used in an amount of 0.1–10 in terms of weight ratio to the other metal.

Further, it is found that the catalyst prepared by adding an oxide, a carbonate, an organic acid salt, a hydroxide or the like of an alkali or alkaline earth metal, for example, sodium hydroxide, calcium carbonate, magnesium oxide, magnesium acetate or the like, or a mixture of two or more of them is particularly improved in both selectivity and reaction activity.

Though the amount of the catalyst used in this invention is not critical, it is preferably in the range of 0.01 to 100 parts by weight per 100 parts by weight of the straight chain lower alcohol.

Said alkali or alkaline earth metal compound is used in an amount of 10 parts by weight or less, preferably 0.01 to 2 parts by weight, per part by weight of the catalyst.

The point of this invention resides in that the above-mentioned catalyst is allowed to exist along with at least one compound selected from the group consisting of mineral acids, heteropoly-acids, heteropoly-acid salts, molybdic acid and organic sulfonic acids. The mineral acids used in this invention include sulfuric acid, hydrochloric acid, nitric acid, phosphoric acid and the like. As said organic sulfonic acid, there may be used p-toluenesulfonic acid and the like. In the heteropoly-acids used in this invention, the condensed coordination element is molybdenum and/or tungsten which may be partially replaced by vanadium, and the central atom is selected from the group consisting of phosphorus, silicon, germanium, titanium, iron, cobalt, nickel, manganese, copper, arsenic, chromium, aluminum, tellurium, iodine, gallium, rhodium, selenium, cerium, and zirconium. As the heteropoly-acid salt, soluble salts of the specific heteropoly-acids mentioned above, for example, alkali metal slts such as lithium salt, sodium salt and the like; alkaline earth metal salts such as magnesium salt and the like; copper salts; cobalt salts; nickel salts; manganese salts; lanthanum salts; zinc salts; aluminum salts; and the like are used.

Among the mineral acids, organic sulfonic acids, heteropoly-acids, heteropoly-acid salts and molybdic acid, there may preferably be used phosphomolybdic acid, phosphotungstic acid, silicotungstic acid, germanomolybdic acid; sodium salts, nickel salts and cobalt salts of these heteropoly-acids; p-toluenesulfonic acid; and molybdic acid. However, weak acids such as phenolic acids, organic carboxylic acids and the like are not effective. From the viewpoint of small formation of by-product, heteropoly-acids and heteropoly-acid salts are particularly preferable.

The oxidation activity tends to drop when the amount of the mineral acid, heteropoly-acid, heteropoly-acid salt, molybdic acid or organic sulfonic acid is small, and side reactions such as addition of the straight chain lower alcohol to the double bond tend to occur markedly when said amount is large. Therefore, the amount of said compound used is preferably 0.1 to 3.0 gram equivalents per liter of the straight chain lower alcohol.

In the reaction of this invention, water is formed with the progress of reaction. Although it is unnecessary to previously add water in the early stage of the reaction, it is also allowable to previously add water in an amount of 0–30% by weight based on the weight of the straight chain lower alcohol.

In this invention, other inert organic solvents may be allowed to exist as a solvent simultaneously with the straight chain lower alcohol. There may be used, for example, at least one member selected from the group consisting of ketones such as acetone, methyl ethyl ketone and the like; esters such as ethyl acetate and the like; ethers such as dioxane, dimethoxyethane, tetrahydrofuran, diethylene glycol diethyl ether and the like; and so on. Though the amount of said organic solvent is not critical, it is preferably 10 times or less in terms of weight ratio to the straight chain lower alcohol.

It is necessary to carry out the reaction under the conditions that the straight chain lower alcohol can be maintained in the liquid phase. The reaction temperature is 150° C. or below, and a sufficient reaction rate can be obtained even in the temperature range of 40° C. to 100° C. The pressure may be such that the straight chain lower alcohol can be maintained in the liquid phase at the reaction temperature. The starting olefin may be in the liquid state or in the gaseous state.

In the practice of this invention, usually known polymerization inhibitors such as hydroquinone or t-butylcatechol may be allowed to exist in a proportion of about 10–1,000 ppm based on the oxidized product.

In carrying out the process of this invention, any of the agitated tank system, fluidized bed system and tricle flow system in which a fixed bed catalyst is employed may be used, and any of the batch system, semi-batch system and continuous system may be used.

In the process of this invention, the formation of by-products such as carbon dioxide and the like is inhibited, the selectivity for unsaturated carboxylic ester is enhanced and the conversion of the starting olefin is also enhanced.

This invention will be explained more specifically below referring to Examples and the accompanying drawings. In the drawings, FIG. 1 indicates the X ray diffraction pattern of the intermetallic compound obtained in Referential Example 1, and FIG. 2 indicates the X ray diffraction pattern of the intermetallic compound obtained in Example 1. This invention is not limited to the Examples. In the Examples, Comparative Examples and Referential Examples, the selectivities for the products were calculated based on propylene or isobutylene.

REFERENTIAL EXAMPLE 1

In 100 ml of acetone was dissolved 5.5 g of bis-benzonitrile-palladium dichloride $[(C_6H_5CN)_2PdCl_2]$, and to the resulting solution was added a solution of 10 g of lead acetate $[(CH_3COO)_2Pb.3H_2O]$ in 70 ml of methanol, upon which brown precipitates were formed. The precipitates were collected by filtration and dried, and 4.5 g of the dried precipitate was dispersed in 50 ml of water. When 4 ml of an aqueous formaldehyde solution and 20 ml of 1 N aqueous sodium hydroxide solution were added to the resulting dispersion, black insolubles were obtained. The insolubles were collected by filtration, washed with water, dried and then subjected to an X ray diffraction test, whereby the product was found to be an intermetallic compound represented by $Pd_3Pb_1$, and its diffraction pattern coincided with that of $Pd_3Pb_1$ in the ASTM card.

The result of the X ray diffraction test of $Pd_3Pb_1$ obtained by the above-mentioned preparation method is shown in FIG. 1 in the accompanying drawings.

In the X ray diffraction test, $CuK_\alpha$ was used as a ray source, and this applies to the Referential Examples and the Examples which appear hereinafter. The measurement of melting point by a differential thermal analysis gave a value of 1220° C. which coincided with the melting point of $Pd_3Pb_1$.

REFERENTIAL EXAMPLE 2

In 100 ml of dilute hydrochloric acid was dissolved 12.8 g of palladium chloride, and to the resulting solution was added 40 ml of an aqueous solution of 9.1 g of lead acetate. The mixture was evaporated to dryness on a water bath, calcined at 300° C. for 3 hours in the air, and then reduced at 300° C. for 12 hours in a stream of hydrogen.

This catalyst was subjected to an X ray diffraction test to find that its major part was an intermetallic compound represented by $Pd_3Pb_1$ though it contained a small quantity of an intermetallic compound represented by $Pd_5Pb_3$. Their diffraction peaks respectively coincided with those of $Pd_3Pb_1$ and $Pd_5Pb_3$ in the ASTM card. No diffraction peaks of metallic palladium were detected.

EXAMPLE 1

Figure 2:
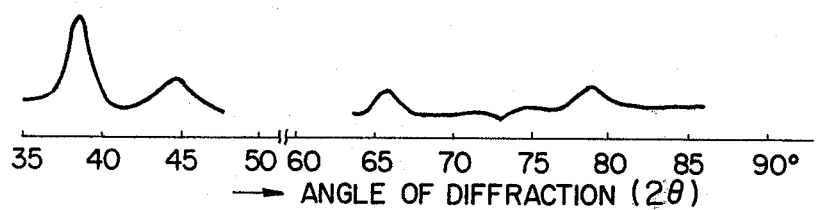

In about 40 ml of water were dissolved 1.76 g of magnesium acetate $[(CH_3COO)_2Mg.4H_2O]$ and 0.92 g of lead acetate $[(CH_3COO)_2Pb.3H_2O]$ were dissolved, and to the resulting solution was added 10 g of silica gel (Fuji Davidson 5D). While stirring the resulting mixture on a boiling water bath, the silica gel was impregnated with the solution. The impregnated product was evaporated to dryness and then calcined at 500° C. for 3 hours in the air. The calcined product was added to a dilute aqueous hydrochloric acid solution containing 0.83 g of palladium chloride $(PdCl_2)$ heated to 60° C., and the mixture was stirred to further impregnate the calcined product with palladium. Then, 2 ml of an aqueous formaldehyde solution and 1 N aqueous sodium hydroxide solution were added, and the supported catalyst thus obtained was collected by filtration, washed with water and dried. This catalyst was subjected to an X ray diffraction test to find that it was an intermetallic compound represented by $Pd_3Pb_1$ ($2\theta=38.6°$, $44.8°$, $65.4°$, $78.6°$) and no diffraction peaks of metallic palladium were detected. The result of the X ray diffraction test is shown in FIG. 2.

Into a 50 ml stainless steel autoclave were charged 0.54 g of this catalyst, 10 ml of methanol, 2.0 g of p-toluenesulfonic acid (the product of Tokyo Kasei Kogyo was used as it was), 1.0 g of propylene and 0.01 mole of oxygen, and the mixture was stirred at 80° C. for 60 minutes at 30 kg/cm$^2$G. As a result, the conversion of propylene was 23.1%, the selectivity for methyl acrylate was 48.7%, the selectivity for acrolein was 45.2% and the selectivity for $CO_2$ was 1.2%.

COMPARATIVE EXAMPLE 1

A catalyst was prepared by the same procedure as in Example 1, except that the lead acetate was not used. With this catalyst, the reaction was carried out under the same conditions as in Example 1. Thus, the conversion of propylene was 14.8%, the selectivity for methyl acrylate was 5.7%, the selectivity for acrolein was 41.6% and the selectivity for $CO_2$ was 4.5%.

COMPARATIVE EXAMPLE 2

The reaction was carried out under the same reaction conditions as in Example 1, except that the p-toluenesulfonic acid was not used. Thus, the conversion of propylene was 0.23%, the selectivity for methyl acrylate was 31.3%, the selectivity for acrolein was 30.4% and the selectivity for $CO_2$ was 2.0%.

COMPARATIVE EXAMPLE 3

The reaction was carried out under the same conditions as in Comparative Example 1, except that the p-toluenesulfonic acid was not used. Thus, the conversion of propylene was 0.22%, the selectivity for methyl acrylate was 6.1%, the selectivity for acrolein was 43.9% and the selectivity for $CO_2$ was 5.6%.

COMPARATIVE EXAMPLE 4

The reaction was carried out under the same conditions as in Comparative Example 3, except that 5% Pd/C (manufactured by Japan Engelhard Co.) was used as the catalyst. Thus, the conversion of propylene was 0.22%, the selectivity for methyl acrylate was 6.0%, the selectivity for acrolein was 41.1% and the selectivity for $CO_2$ was 5.6%.

EXAMPLE 2

An alumina-supported catalyst was prepared by the same procedure as in Example 1, except that γ-alumina (Neobead, a trade name of Mizusawa Kagaku) was used as the carrier and the amount of palladium used was 0.42 g.

Then, the reaction was carried out under the same reaction conditions as in Example 1, except that the above-mentioned γ-alumina-supported catalyst was used as the catalyst. Thus, the conversion of propylene was 25.3%, the selectivity for methyl acrylate was 49.7%, the selectivity for acrolein was 44.2% and the selectivity for $CO_2$ was 1.2%.

EXAMPLES 3 TO 6

Catalysts were prepared under the same conditions as in Example 2, except that the 0.92 g of lead acetate was replaced by 0.57 g of bismuth oxide dissolved in dilute hydrochloric acid (Example 3), 0.65 g of thallium (I) nitrate (Example 4), 0.28 g of telluric acid (Example 5) or 0.77 g of mercuric acetate (Example 6), and the reaction was carried out under the same reaction conditions as in Example 2 using the catalyst prepared above. The results obtained were as shown in Table 1.

TABLE 1

| Example No. | Conversion of propylene (%) | Selectivity for methyl acrylate (%) | Selectivity for acrolein (%) | Selectivity for $CO_2$ (%) |
| --- | --- | --- | --- | --- |
| 3 | 24.2 | 49.3 | 44.9 | 1.2 |
| 4 | 20.0 | 49.1 | 45.0 | 1.2 |
| 5 | 19.0 | 48.6 | 44.7 | 1.3 |
| 6 | 19.6 | 49.0 | 43.8 | 1.2 |

EXAMPLE 7

The reaction was carried out under the same conditions as in Example 2, except that the 2 g of p-toluenesulfonic acid was replaced by 2 g of sodium phosphomolybdate. Thus, the conversion of propylene was 23.4%, the selectivity for methyl acrylate was 42.6%, the selectivity for acrolein was 42.4% and the selectivity for $CO_2$ was 1.1%.

EXAMPLES 8 TO 11

The reaction was carried out under the same conditions as in Example 2, except that the 2.0 g of p-toluenesulfonic acid was replaced by 2.0 g of trifluoromethanesulfonic acid, 1.0 g of concentrated sulfuric acid, 1.0 g of concentrated hydrochloric acid or 1.0 g of concentrated nitric acid. The results obtained are shown in Table 2.

TABLE 2

| Example No. | Additive | Conversion of propylene (%) | Selectivity for methyl acrylate (%) | Selectivity for acrolein (%) | Selectivity for $CO_2$ (%) |
| --- | --- | --- | --- | --- | --- |
| 8 | Trifluoro methanesulfonic acid | 24.0 | 49.1 | 44.4 | 1.2 |
| 9 | Concentrated sulfuric acid | 24.5 | 52.9 | 40.1 | 1.2 |
| 10 | Concentrated hydrochloric acid | 22.3 | 49.3 | 44.0 | 1.2 |
| 11 | Concentrated nitric acid | 21.6 | 48.0 | 44.9 | 1.3 |

EXAMPLES 12 TO 21

The reaction was carried out under the same conditions as in Example 7, except that the sodium phosphomolybdate was replaced by phosphomolybdic acid, phosphotungstic acid, silicotungstic acid, germanomolybdic acid, silicomolybdic acid, germanotungstic acid, cobalt phosphomolybdate, nickel silicotungstate, copper phosphotungstate or molybdenum trioxide. The results obtained are shown in Table 3.

TABLE 3

| Example No. | Additive | Conversion of propylene (%) | Selectivity for methyl acrylate (%) | Selectivity for acrolein (%) | Selectivity for $CO_2$ (%) |
|---|---|---|---|---|---|
| 12 | Phosphomolybdic acid | 19.3 | 34.9 | 45.6 | 1.0 |
| 13 | Phosphotungstic acid | 18.1 | 36.8 | 43.1 | 1.0 |
| 14 | Silicotungstic acid | 18.5 | 45.1 | 39.1 | 1.1 |
| 15 | Germanomolybdic acid | 19.1 | 37.6 | 45.0 | 1.1 |
| 16 | Silicomolybdic acid | 16.2 | 30.2 | 47.4 | 1.0 |
| 17 | Germanotungstic acid | 19.0 | 35.3 | 46.3 | 1.1 |
| 18 | Cobalt phosphomolybdate | 23.5 | 46.3 | 39.7 | 1.1 |
| 19 | Nickel silicotungstate | 21.6 | 40.0 | 42.6 | 1.1 |
| 20 | Copper phosphotungstate | 21.5 | 39.6 | 41.0 | 1.1 |
| 21 | Molybdenum trioxide | 15.1 | 28.0 | 47.6 | 1.0 |

EXAMPLE 22

The reaction was carried out under the same conditions as in Example 2, except that the methanol was replaced by 10 ml of ethanol. The results obtained are shown in Table 4.

TABLE 4

| Example No. | Straight chain lower alcohol | Conversion of propylene (%) | Selectivity for acrylic ester (%) | Selectivity for acrolein (%) | Selectivity for $CO_2$ (%) |
|---|---|---|---|---|---|
| 22 | Ethanol | 10.6 | 28.4 | 43.7 | 1.2 |

EXAMPLE 23

The reaction was carried out under the same conditions as in Example 2, except that the propylene was replaced by isobutylene and the temperature was changed from 80° C. to 100° C. and the pressure was varied from 30 kg/cm²G to 20 kg/cm²G. As a result, the conversion of isobutylene was 25.0%, the selectivity for methyl methacrylate was 34.8%, the selectivity for methacrolein was 50.1% and the selectivity for $CO_2$ was 1.0%.

EXAMPLES 24 TO 28

The reaction was carried out under the same conditions as in Example 1, except that the 2.0 g of p-toluenesulfonic acid was replaced by 0.0019 g, 0.019 g, 0.19 g, 5.7 g or 9.5 g of p-toluenesulfonic acid (the product of Tokyo Kasei Kogyo was used as it was). The results obtained are shown in Table 5.

TABLE 5

| Example No. | Amount of p-toluenesulfonic acid charged (g) | Conversion of propylene (%) | Selectivity for methyl acrylate (%) | Selectivity for acrolein (%) | Selectivity for $CO_2$ (%) |
|---|---|---|---|---|---|
| 24 | 0.0019 | 0.9 | 48.1 | 45.6 | 1.2 |
| 25 | 0.019 | 3.6 | 47.8 | 45.0 | 1.2 |
| 26 | 0.19 | 19.8 | 48.7 | 45.4 | 1.2 |
| 27 | 5.7 | 23.0 | 48.5 | 44.9 | 1.2 |
| 28 | 9.5 | 23.5 | 31.3 | 38.5 | 1.5 |

EXAMPLES 29 TO 32

Catalysts were prepared under the same conditions as in Example 2, except that the 0.92 g of lead acetate was replaced by 0.0046 g, 0.046 g, 4.6 g or 9.2 g of lead acetate. With the catalysts, the reaction was carried out under the same conditions as in Example 2. The results obtained are shown in Table 6.

TABLE 6

| Example No. | Lead acetate (g) | Conversion of propylene (%) | Selectivity for methyl acrylate (%) | Selectivity for acrolein (%) | Selectivity for $CO_2$ (%) |
|---|---|---|---|---|---|
| 29 | 0.0046 | 22.4 | 3.7 | 81.0 | 4.7 |
| 30 | 0.046 | 22.3 | 47.9 | 45.1 | 1.2 |
| 31 | 4.6 | 19.5 | 48.1 | 44.5 | 1.2 |
| 32 | 9.2 | 7.4 | 48.3 | 40.6 | 1.3 |

EXAMPLE 33

A stainless steel reactor tube of 10 mm in inner diameter was packed with the same catalyst as in Example 2, and methanol containing 10% by weight of p-toluenesulfonic acid was fed to the reactor at a rate of 40 g/hr and, at the same time, a gaseous mixture comprising 7% by volume of propylene, 10% by volume of oxygen and 83% by volume of helium was fed to the reactor at a rate of 12 liters/hr. The inner space of the reactor was kept at a temperature of 65° C. and a pressure of 12 kg/cm²G. Ten hours after the start of the reaction, the conversion of propylene was 21.0%, the selectivity for methyl acrylate was 75.3% and the selectivity for $CO_2$ was 0.9%.

EXAMPLE 34

A catalyst was prepared under the same conditions as in Example 2, except that the magnesium acetate was not used. With the catalyst, the reaction was carried out under the same conditions as in Example 2. As a result, the conversion of propylene was 19.9%, the selectivity for methyl acrylate was 42.9%, the selectivity for acrolein was 45.1% and the selectivity for $CO_2$ was 1.4%.

What is claimed is:

1. A process for producing an ester of acrylic or methacrylic acid by oxidizing propylene or isobutylene in the liquid phase in the presence of a straight chain lower alcohol and molecular oxygen, characterized by effecting the reaction at 150° C. or below in the presence of
   (1) a catalyst consisting of palladium and at least one metal selected from the group consisting of lead, bismuth, thallium, tellurium and mercury, and
   (2) at least one compound selected from the group consisting of mineral acids, heteropoly-acids, heteropoly-acid salts, molybdic acid and organic sulfonic acids.

2. A process according to claim 1, wherein the catalyst (1) is an intermetallic compound of palladium and at least one metal selected from the group consisting of lead, bismuth, thallium, tellurium and mercury.

3. A process according to claim 1 or 2, wherein the catalyst (1) is composed of palladium and lead, bismuth or both of them.

4. A process according to claim 1, wherein the catalyst (1) is used in a proportion of 0.01–100 parts by weight per 100 parts by weight of said straight chain lower alcohol.

5. A process according to claim 1, wherein the compound (2) is a heteropoly-acid or a heteropoly-acid salt.

6. A process according to claim 5, wherein said heteropoly-acid contains molybdenum, tungsten or both of them as its condensed coordination element and contains one element selected from the group consisting of phosphorus, silicon, germanium, titanium, iron, cobalt, nickel, manganese, copper, arsenic, chromium, aluminum, tellurium, iodine, gallium, rhodium, selenium, cerium and zirconium as its central element and said heteropoly-acid salt is an alkali metal salt, an alkaline earth metal salt, a copper salt, a cobalt salt, a nickel salt, a manganese salt, a lanthanum salt, a zinc salt or an aluminum salt of the above-mentioned heteropoly-acid.

7. A process according to claim 1, wherein the compound (2) is selected from the group consisting of phosphomolybdic acid, phosphotungstic acid, silico-tungstic acid, germanomolybdic acid; sodium salts, nickel salts and cobalt salts of these heteropoly-acids; p-toluenesulfonic acid; and molybdic acid.

8. A process according to claim 1, wherein the compound (2) is used in an amount of 0.1–3.0 gram equivalents per liter of said straight chain lower alcohol.

9. A process according to claim 1, 2, 4, 5 or 8, wherein (3) at least one compound selected from the group consisting of alkali metal compounds and alkaline earth metal compounds is allowed to exist in the reaction system together with the catalyst (1) and the compound (2).

10. A process according to claim 9, wherein the compound (3) is used in an amount of not more than 10 times the weight of the catalyst (1).

11. A process according to claim 9, wherein the compound (3) is used in an amount of 0.01 to 2 times the weight of the catalyst (1).

12. A process according to claim 9, wherein the compound (3) is an oxide, a carbonate, an organic acid salt or a hydroxide of an alkali or alkaline earth metal.

13. A process according to claim 1 or 4, wherein the weight ratio of palladium to the other metal in the catalyst (1) is in the range of from 0.1 to 10.

14. A process according to claim 1, wherein said straight chain lower alcohol is methanol, ethanol, 1-propanol or 1-butanol.

15. A process according to claim 1, wherein said straight chain lower alcohol is methanol.

16. A process according to claim 1, 14 or 15, wherein the amount of said straight chain lower alcohol is 1 mole or more per mole of propylene or isobutylene.

17. A process according to claim 1, wherein the reaction is carried out under a pressure of at least 12 kg/cm$^2$ so that said straight chain lower alcohol is maintained in the liquid phase.

18. A process according to claim 17, wherein the reaction temperature is a temperature in the range of from 40° to 100° C.

* * * * *

UNITED STATES PATENT AND TRADEMARK OFFICE
CERTIFICATE OF CORRECTION

PATENT NO. : 4,356,316

DATED : October 26, 1982

INVENTOR(S) : Atsushi Aoshima et al

It is certified that error appears in the above-identified patent and that said Letters Patent is hereby corrected as shown below:

The title page should be deleted to appear as per attached title page.

Signed and Sealed this

Tenth Day of May 1983

[SEAL]

Attest:

Attesting Officer

GERALD J. MOSSINGHOFF

Commissioner of Patents and Trademarks

United States Patent [19]

Aoshima et al.

[11] 4,356,316

[45] Oct. 26, 1982

[54] PROCESS FOR PRODUCING UNSATURATED CARBOXYLIC ESTERS

[75] Inventors: Atsushi Aoshima, Yokohama; Toshiaki Murofushi, Fuji, both of Japan

[73] Assignee: Asahi Kasei Kogyo Kabushiki Kaisha, Osaka, Japan

[21] Appl. No.: 236,956

[22] Filed: Feb. 23, 1981

[30] Foreign Application Priority Data

Mar. 5, 1980 [JP] Japan ............................. 55-26759
Apr. 22, 1980 [JP] Japan ............................. 55-53154

[51] Int. Cl.³ .......................................... C07C 67/39
[52] U.S. Cl. ................................... 560/208; 252/439; 252/434; 252/435; 252/436; 252/430; 252/437; 252/455 R; 252/456; 252/457; 252/458; 252/460
[58] Field of Search ................. 560/208; 568/470, 478

[56] References Cited

U.S. PATENT DOCUMENTS

| | | | |
|---|---|---|---|
| 3,485,877 | 12/1969 | Hargis et al. ................. | 568/478 |
| 3,658,886 | 4/1972 | Sennewald et al. ............ | 560/208 |
| 3,925,463 | 12/1975 | Ferlazzo et al. .............. | 560/208 |
| 4,248,019 | 2/1981 | Tamura et al. ................ | 560/208 |

OTHER PUBLICATIONS

Kurakina, T. V. et al., *Chemical Abstracts*, vol. 86, (1977), #83233c.

*Primary Examiner*—Natalie Trousof
*Assistant Examiner*—L. Hendriksen
*Attorney, Agent, or Firm*—Sprung, Horn, Kramer & Woods

[57] ABSTRACT

A process for producing an ester of acrylic or methacrylic acid by oxidizing propylene or isobutylene in the liquid phase in the presence of a straight chain lower alcohol and molecular oxygen, characterized by carrying out the reaction in the presence of:

(1) a catalyst consisting of palladium and at least one metal selected from the group consisting of lead, bismuth, thallium, tellurium and mercury, preferably an intermetallic compound of palladium and said metal;

(2) at least one compound selected from the group consisting of mineral acids, heteropoly-acids, heteropoly-acid salts, molybdic acid and organic sulfonic acids, preferably heteropoly-acids or their salts; and (3) optionally, at least one compound selected from the group consisting of alkali metal compounds and alkaline earth metal compounds.

According to this process, the activity of catalyst is high even in a reaction at low temperatures, the amount of by-product is small and the objective ester can be produced with a high selectivity.

18 Claims, 2 Drawing Figures